United States Patent

Amstutz

[11] Patent Number: 6,063,124
[45] Date of Patent: May 16, 2000

[54] ACETABULAR CUP PROSTHESIS INSERTION AND REMOVAL ASSEMBLY AND TECHNIQUE

[76] Inventor: Harlan C. Amstutz, 900 Napoli Dr., Pacific Palisades, Calif. 90272

[21] Appl. No.: 09/260,163

[22] Filed: Mar. 1, 1999

[51] Int. Cl.[7] .................................................. A61F 2/32
[52] U.S. Cl. ................................................... 623/22
[58] Field of Search ............................... 623/21, 22, 19, 623/18; 606/91

[56] References Cited

U.S. PATENT DOCUMENTS

| | | |
|---|---|---|
| 3,840,904 | 10/1974 | Tronzo . |
| 4,101,985 | 7/1978 | Baumann et al. . |
| 4,123,806 | 11/1978 | Amstutz et al. . |
| 4,715,860 | 12/1987 | Amstutz et al. . |
| 4,752,296 | 6/1988 | Buechel et al. . |
| 5,037,424 | 8/1991 | Aboczsky . |
| 5,169,399 | 12/1992 | Ryland et al. ............................. 606/91 |
| 5,250,051 | 10/1993 | Maryan . |
| 5,417,696 | 5/1995 | Kashuba et al. ........................... 606/91 |
| 5,486,181 | 1/1996 | Cohen et al. ............................... 606/91 |
| 5,540,697 | 7/1996 | Rehmann et al. .......................... 606/91 |
| 5,658,294 | 8/1997 | Sederholm ................................. 623/22 |
| 5,683,399 | 11/1997 | Jones . |
| 5,904,688 | 5/1999 | Gilbert et al. .............................. 606/91 |

OTHER PUBLICATIONS

Wright Medical Techonology Brochure Entitled "Femoral Surface Replacement System".

*Primary Examiner*—Jeffrey A. Smith
*Assistant Examiner*—Eduardo C. Robert
*Attorney, Agent, or Firm*—Oppenheimer Wolff & Donnelly LLP

[57] ABSTRACT

An exemplary acetabular cup prosthesis insertion and removal assembly includes a bayonet coupler that has fingers for extending into recesses of an acetabular cup to hold the cup onto the coupler. A holder-driver member is secured to the bayonet coupler, and has an enlarged head for receiving impacts. A securing member for engaging the inner surface of the acetabular cup is adjustably mounted to the holder-driver member to apply a biasing force to urge the cup away from the holder-driver member and the bayonet coupler, thereby firmly holding the cup onto the coupler. An alignment guide assembly with at least one guiding arm or member may be mounted on the holder-driver member to facilitate accurate placement of the acetabular cup. A slap-hammer or extractor is also provided and may be attached to the holder-driver member to remove an acetabular cup that is initially misplaced in the acetabulum.

13 Claims, 8 Drawing Sheets

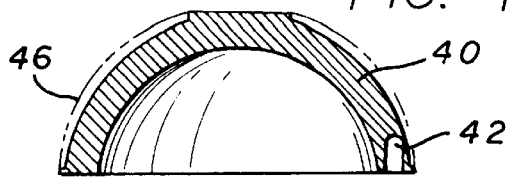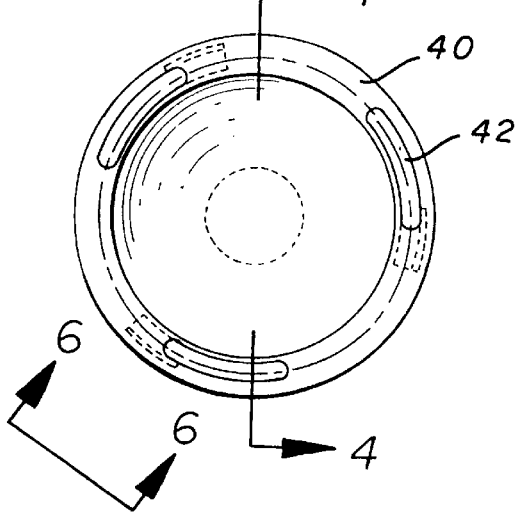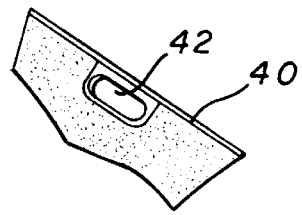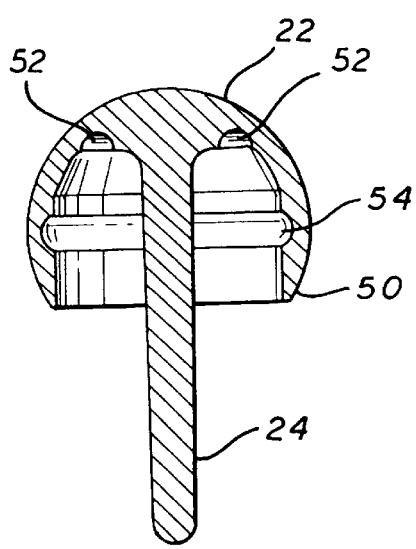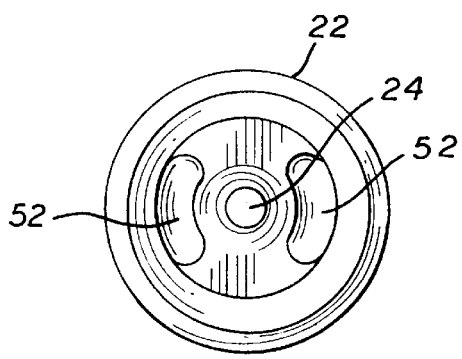

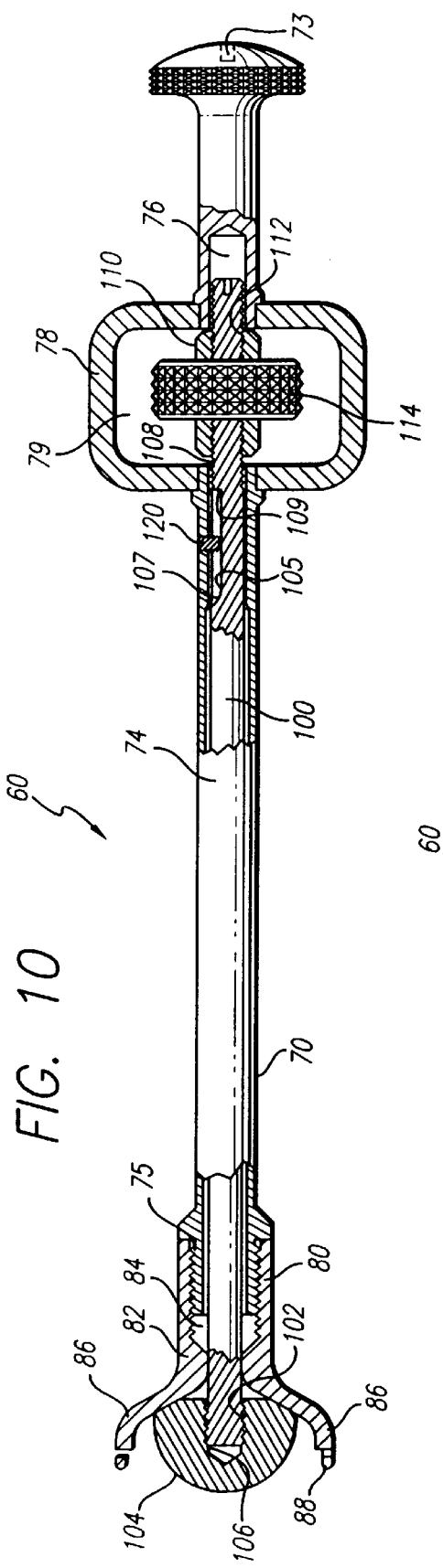
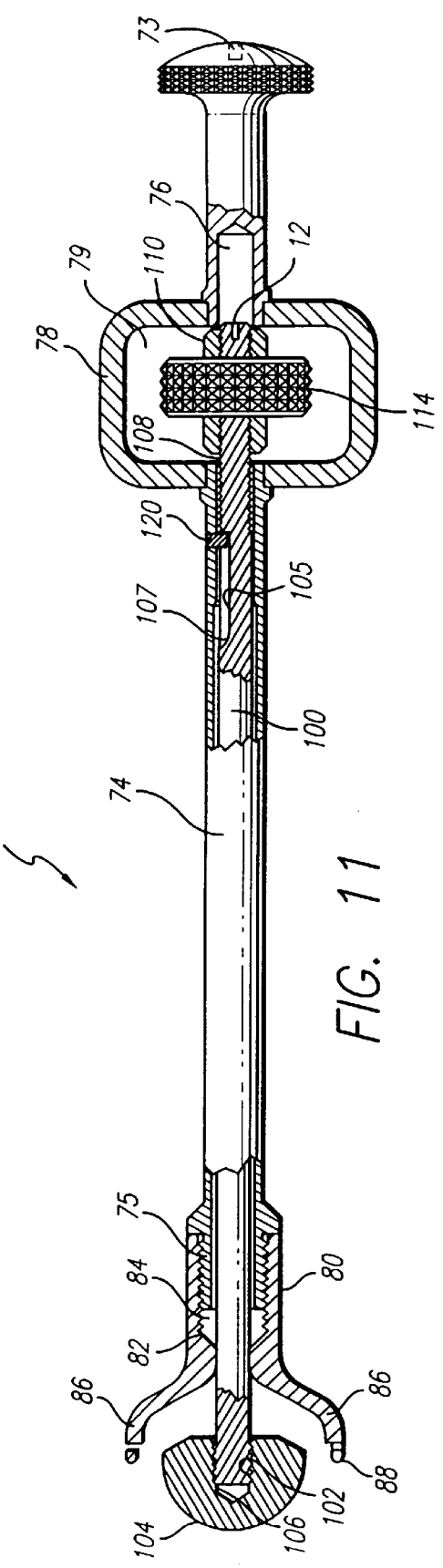

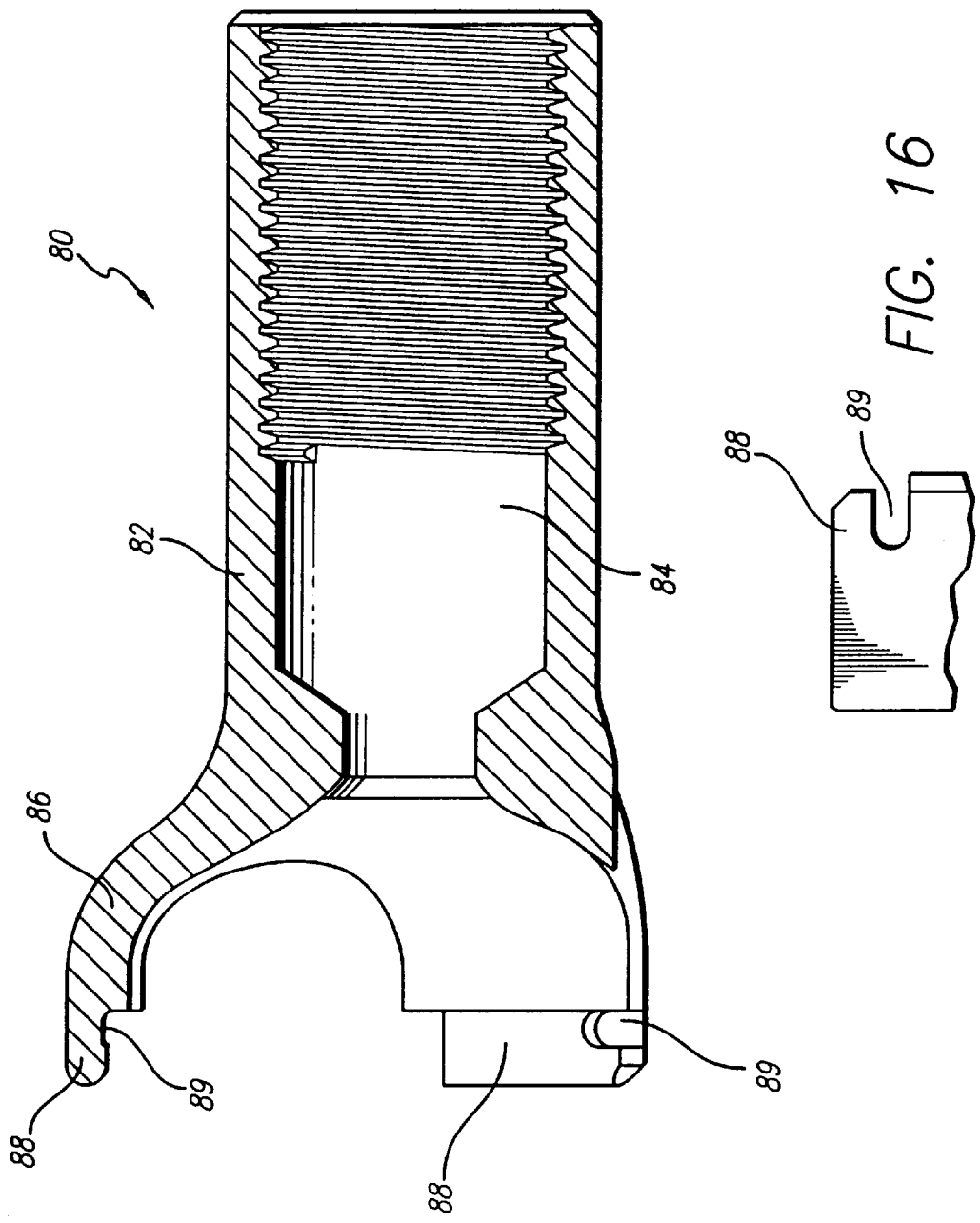

ACETABULAR CUP PROSTHESIS INSERTION AND REMOVAL ASSEMBLY AND TECHNIQUE

FIELD OF THE INVENTION

The present invention relates generally to hip joint replacement prostheses, and particularly to the construction and use of an acetabular cup prothesis insertion and removal assembly and technique.

BACKGROUND OF THE INVENTION

When severe hip joint problems are encountered, it is sometimes necessary to replace the hip joint, either the ball or the socket or both. The large upper leg bone, or femur, has a long lower main portion, with a head or ball connected by a neck portion angled inward toward the hip socket from the upper end of the main portion of the femur.

One generally used hip joint replacement technique involved removal of the head and neck of the femur, and the insertion of a long angled and tapered metal prosthesis into the central "intramedulary" canal at the open upper end of the main straight portion of the femur. This femoral prosthesis typically has a relatively small metal ball at its upper end which mated with small plastic socket mounted on the hip side of the joint.

The aforementioned "total" hip replacement technique was drastic since it involved complete removal of the head and neck of the femur, and made any subsequent hip joint problems difficult to handle.

On the socket side of the joint, referred to as the "acetabular" in medical parlance, some prostheses were employed which used a plastic cup to mate with the femoral component; and it has been determined that these plastic acetabular components were subject to considerable wear, producing particulate matter which adversely affected the lifetime of the hip joint prosthesis. Metal-to-metal joints were also proposed in the 1960s, but lack of accuracy in sphericity and other problems had prevented their wide acceptance.

As shown in U.S. Pat. No. 4,123,806, granted Nov. 7, 1978, an early femoral prosthesis involved a cobalt-chromium-molybdenum metallic shell of generally hemispherical shape, designed on the principle of removing all non-viable femoral head bone, but also preserving as much of the head and neck as possible. A polyethylene socket or acetabular component was employed. The femoral shell was cemented onto the head of the femur, following shaping to one of several standard sizes. This surface replacement conserved bone and permitted a full femoral hip replacement if problems arose with initial replacement prosthesis. However, in several cases the polyethylene wear and resultant particulate material caused loosening of the femoral shell and/or the acetabular shell.

In a more recent prior art development, as described in a publication entitled "Femoral Surface Replacement System, Surgical Technique," a metal-to-metal hip joint prosthesis has been employed, using a relatively thin all-metal socket prosthesis secured in place by bone ingrowth; and a cemented metal shell as the femoral component. However, the results have, on occasion, not been quite as good as would be desirable, and occasional problems have arisen with regard to accurately positioning the femoral shell, and providing the very uniform layer of cement between the femoral head and the metal shell, which is desirable for firm securing and long life of the prosthesis and/or for preventing notching of the neck which could lead to femoral neck fracture. It is also noted that metal-to-metal hip joint prostheses have been tried heretofore, but have not been entirely satisfactory, with clicking and ratcheting noises occurring in some cases, and with the potential increased torque causing loosening.

There have also been prior attempts to provide instruments for implanting an acetabular cup prothesis into a patient's acetabulum. For example, U.S. Pat. No. 5,037,424, issued to R. I. Aboczsky on Aug. 6, 1991, discloses an "Instrument for Orienting, Inserting And Impacting an Acetabular Cup Prosthesis". The Aboczsky assembly includes an impact rod that has a shaped-end base, and a coupling rod affixed to and angularly extended from the base. The coupling rod and the base cooperate to grip an attached acetabular cup for insertion, alignment, and impaction. The Aboczsky assembly also includes an alignment bar to guide a physician or user in placing the acetabular cup. When the acetabular cup is properly placed in the patient's acetabulum, the alignment bar should be aligned normal to a line which crosses from the patient's posterior superior iliac to the anterior superior iliac. After the cup is properly inserted and placed, the assembly is impacted to seat the cup in the acetabulum. However, the Aboczsky assembly does not include a structure or mechanism to readily remove a misplaced acetabular cup. Furthermore, the end of the impact rod is generally not shaped to provide an ideal surface for receiving impacts.

Accordingly, it is highly desirable to provide an improved acetabular cup prosthesis assembly and technique for inserting and removing an acetabular cup prosthesis.

BRIEF SUMMARY OF THE INVENTION

An exemplary acetabular cup prosthesis insertion and removal assembly includes a bayonet coupler that has fingers for extending into recesses of an acetabular cup to hold the cup onto the coupler. A holder-driver member is secured to the bayonet coupler, and has an enlarged head for receiving impacts. A securing member for engaging the inner surface of the acetabular cup is adjustably mounted to the holder-driver member to apply a biasing force to the cup to urge it away from the holder-driver member and the bayonet coupler to thereby firmly hold the cup onto the coupler.

In accordance with a preferred embodiment, the holder-driver member has first and second tubular portions that are connected by a linking member, and a head generally shaped to provide an impact surface. The first and second tubular portions are aligned such that a support extension may be passed through the first tubular portion into the second tubular portion. An adjustment member is mounted on the outer end of the extension to allow the extension to be retracted or extended. The securing member is secured to the opposite end of the support extension, and preferably has a substantially hemispherical shape to engage the inner surface of the acetabular cup.

An alignment guide assembly having at least one guiding arm or member can be mounted on the holder-driver member to facilitate accurate placement of the acetabular cup.

In implanting the acetabular cup into a patient's acetabulum, the user or orthopaedic surgeon disposes the holder-driver member such that the guiding arms of the alignment guide assembly are generally perpendicular to the patient who is lying horizontally on his or her side. With the patient lying horizontally, and with guiding arms at angles of about forty two and twenty degrees with the holder-driver member, the acetabular cup will be appropriately directed upward and to the rear at the proper angles. In short, the alignment guide assembly helps the user to accurately place and align the cup in the acetabulum.

After the cup is properly placed and aligned, the user may firmly tap the head of the holder-driver member with an impacting tool, such as a mallet, to firmly seat the cup in the acetabulum. Once the cup is firmly seated, the user may actuate the adjustment member to disengage the securing member from the cup and remove the assembly from the cup without dislodging it from the acetabulum.

A slap-hammer or extractor may be attached to the holder-driver member to remove an acetabular cup that is initially misplaced in the acetabulum. After its removal, the cup may be reoriented and relocated.

The above described and many other features and attendant advantages of the present invention will become apparent as the invention becomes better understood from a consideration of the following detailed description, and from the accompanying drawings.

BRIEF DESCRIPTION OF SEVERAL VIEWS OF THE DRAWINGS

FIGS. 4, 5 and 6 are detailed views showing the construction of the metallic acetabular cup prosthesis;

FIGS. 7 and 8 are cross-sectional and bottom plan views, respectively, of the femoral prosthesis;

FIG. 10 is a fragmentary side view of the acetabular cup prosthesis insertion and removal assembly shown in FIG. 9, without the acetabular cup and alignment guide assembly, and with the support extension fully retracted;

FIG. 11 is a fragmentary side view of the acetabular cup prosthesis insertion and removal assembly shown in FIG. 9, without the acetabular cup and alignment guide assembly, and with the support extension fully extended;

FIG. 15 is a cross-sectional view of the bayonet coupler taken along line 15—15 in FIG. 14;

FIG. 16 is a cross-sectional view of the bayonet coupler taken along line 16—16 in FIG. 14.

DETAILED DESCRIPTION OF PREFERRED EMBODIMENTS

The present invention discloses the construction and use of a novel acetabular cup prosthesis insertion and removal assembly. The following detailed description is provided to enable any person skilled in the art to make and use the invention and to set forth the best modes contemplated by the inventor for carrying out the invention. This description is not to be taken in a limiting sense, but is made merely for the purpose of illustrating the general principles of the invention.

Figure 1:
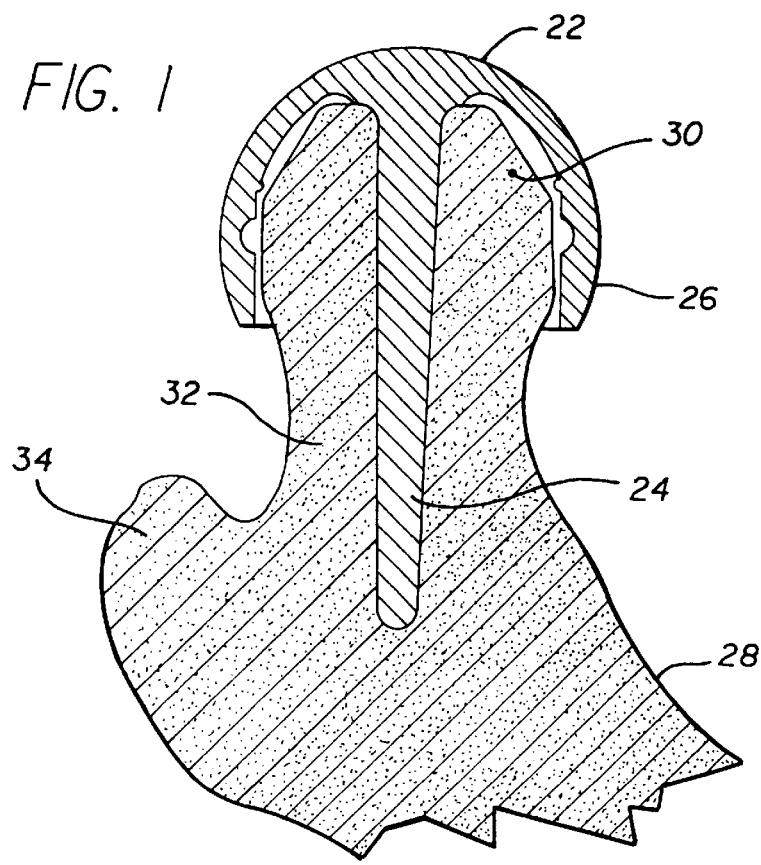
FIG. 1 is a cross-sectional view of a metallic femoral surface replacement prosthesis prior to cement fixation.

Referring more particularly to the drawings, FIG. 1 shows a cross-sectional view of a hard metallic femoral prosthesis 22 of the surface replacement type. The femoral prosthesis 22 includes a central tapered stem 24 and a spherical surface replacement portion 26. The prosthesis 22 is shown mounted on the upper end of the femur 28, or thigh-bone, which is the large leg bone located above the knee. The upper portion of the femur 28 includes a head or ball portion 30, a neck 32, and the trochanter 34. Incidentally, the trochanter is a boney protuberance from the femur to which major muscle groups are secured for controlling the motion of the leg, for example. In certain prior femoral surface replacement procedures, the trochanter was removed to give more access for the operating procedure, and subsequently reattached; however, using the present surgical techniques, the undesired removal and reattachment of the trocanter are no longer necessary.

Returning to the femoral prosthesis 22, it has an extent which is slightly greater than a hemisphere to cover all of the reamed bone of the femoral head, and the central tapered stem 24 extends from the center of the spherical shell 26 into the head and neck of the femur beyond the lower edge or skirt of the prosthesis a distance slightly greater than the distance from the upper end of the prosthesis 22 to the edge of the skirt. The femoral prosthesis 22 is made of known high strength biologically inert metallic materials such as a cobalt chrome alloy.

Figure 2:
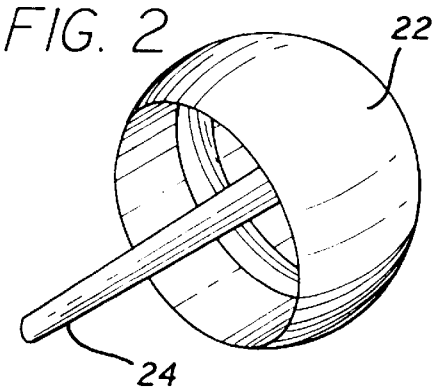
FIGS. 2 and 3 are perspective views of the mating femoral ball (head) and acetabular cup (socket) prostheses.
Figure 3:
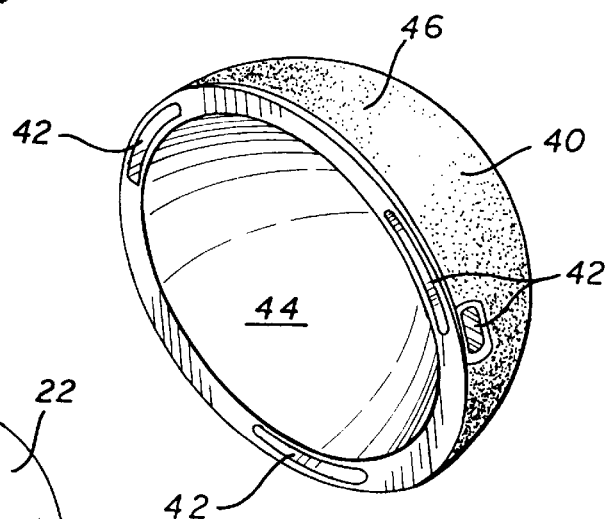

FIGS. 2 and 3 of the drawings are perspective views of the femoral prosthesis 22, and the acetabular cup or socket prosthesis 40. Regarding the acetabular cup prosthesis 40, at its edges it includes openings or recesses 42 to which tooling may be secured in order to mount the acetabular cup prosthesis in place, and on rare occasions to remove it. The prosthesis 40 has an outer surface which is formed of fine granular sintered material, preferably of a cobalt chrome alloy of a known type, which encourages bone ingrowth. It is approximately ½ centimeter or 5 millimeters in thickness. The interior surface 44 of the acetabular component 40 is generally spherical in its configuration. The spherical surface 44 mates with the outer spherical surface configuration of the femoral prosthesis 22, with a tolerance of between one and five microns or preferably between one and two or three microns, where a micron is equal to one one-thousandth of a millimeter (0.001 mm). The very accurate machining or grinding of the outer surface of the femoral component 22 and the inner surface 44 of the acetabular component 40 are very useful in the use of the metal-to-metal prosthesis as described in the present specification. The clearance between the femoral and the acetabular components is preferably about 125 to 250 microns, with larger size assemblies having larger tolerances. This spacing permits lubrication of the surfaces by the patient's normal synovial fluid. These accurately machined prostheses are available in successive sizes ranging from 36 to 54 millimeters, in two millimeter increments, from Wright Medical Technology, Inc., 5677 Airline Road, Arlington, Tenn. 38002. The surgical equipment disclosed in this specification may also be purchased from Wright Medical Technology, Inc.

FIGS. 4, 5 and 6 are detailed mechanical drawings of the acetabular cup or socket prosthesis 40. FIGS. 4, 5 and 6 show the preferred configuration of the securing openings 42, and also the location of the sintered beads 46 which are on the outer surface of the hemispherical configuration of the prosthesis 40.

FIGS. 7 and 8 are cross-sectional and lower plan views, respectively, of the femoral prosthesis 22. The femoral prosthesis 22 includes the outer spherical surface 26 which extends for somewhat more than a hemisphere, and has a lower edge or skirt 50. Within the femoral prosthesis 22 are recesses 52 which tend to resist rotation of the prosthesis once it is secured in place with cement. In addition, the circular recess 54 is useful for resisting axial shifting of the position of the femoral prosthesis once it is cemented in place.

Figure 9:
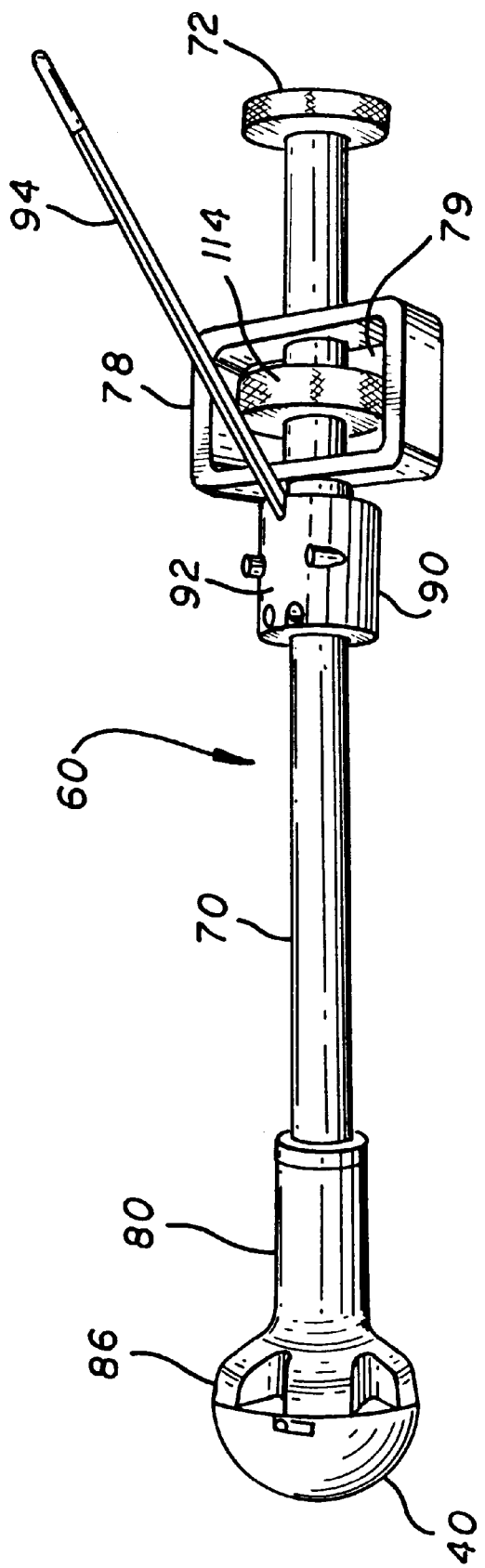
FIG. 9 shows an exemplary acetabular cup prosthesis insertion and removal assembly, with an acetabular cup attached to a bayonet coupler.
Figure 12:
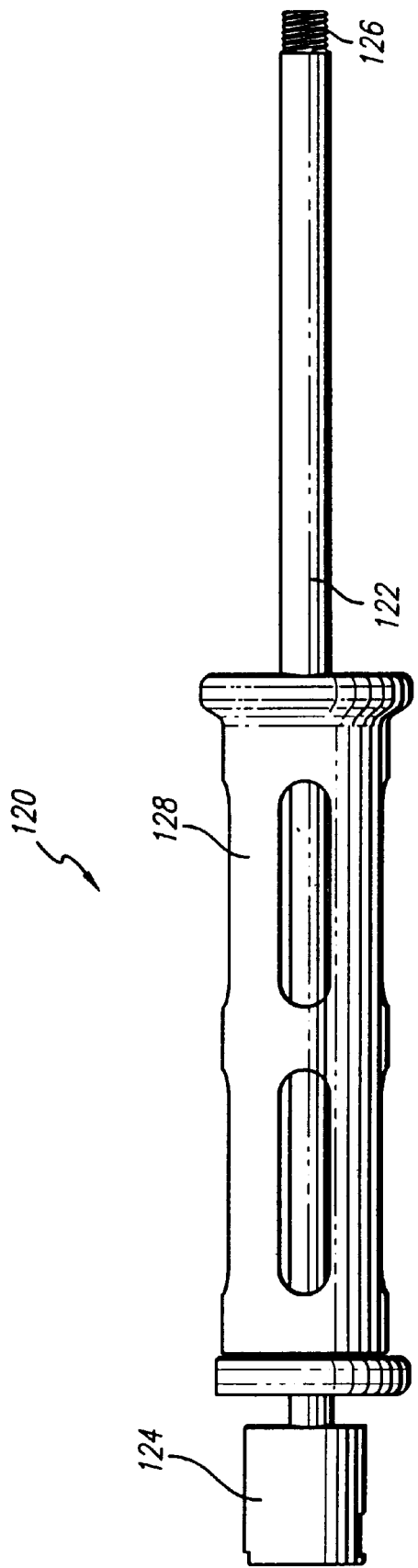
FIG. 12 shows a side view of an exemplary slap-hammer or extractor.
Figure 17:
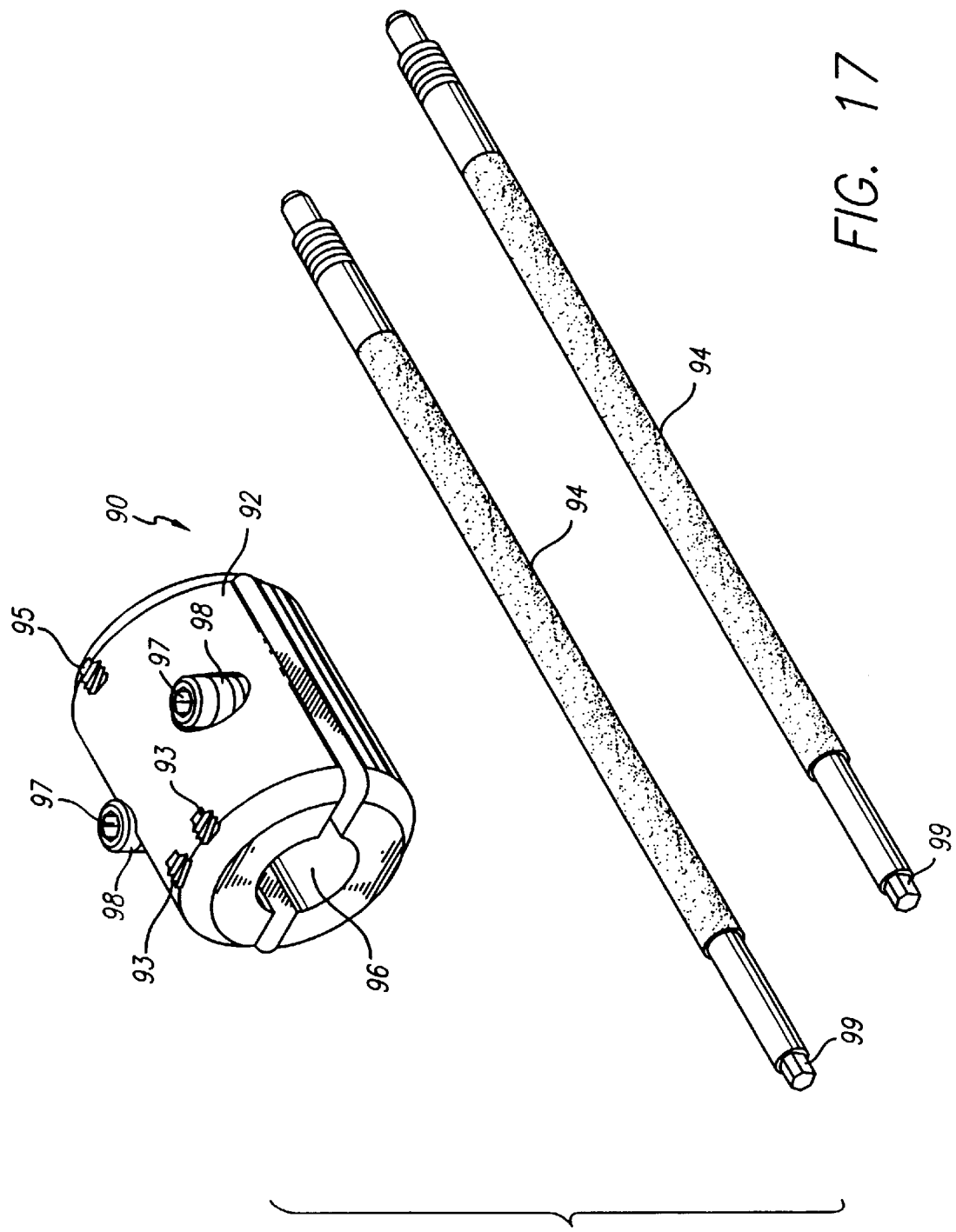
FIG. 17 shows an exploded perspective view of an exemplary alignment guide assembly.

Turning now to FIG. 9, FIG. 9 shows an assembled acetabular cup prosthesis insertion and removal assembly 60. The assembly 60 includes (1) a holder-driver member 70 having at one end a head 72 that is generally shaped to receive impacts, (2) a bayonet coupler 80 secured to the opposite end of the holder-driver member 70, and (3) an alignment guide assembly 90 with a guiding arm 94 is mounted on the holder-driver member 70. It should be noted that the alignment guide assembly 90, as shown in FIG. 17, may include more than one guiding arms 94. FIG. 9 also shows an acetabular cup prosthesis 40 attached to the bayonet coupler 80. The assembly 60 is generally used for inserting, aligning, and impacting the acetabular cup 40 to firmly seat it in a patient's acetabulum. A slap-hammer or extractor 120, as shown in FIG. 12, may also be attached to the holder-driver member 70 to remove an incorrectly placed acetabular cup 40 from the acetabulum.

In implanting the acetabular cup into a patient's acetabulum, the user or orthopaedic surgeon disposes the holder-driver member 70 such that the guiding arms 94 of the alignment guide assembly 90 are generally perpendicular to the patient who is lying horizontally on his or her side. With the patient lying horizontally, and with guiding arms 94 at angles of about forty two and twenty degrees relative to the holder-driver member, the acetabular cup will be appropriately directed upward and to the rear at proper angles. In short, the alignment guide assembly 90 aids the user or surgeon in accurately placing and aligning the cup in the patient's acetabulum.

Once the acetabular cup 40 is properly placed and aligned, the user may firmly tap the head 72 of the holder-driver member 70 with an impacting tool, such as a mallet (not shown), to press fit the cup 40 firmly in the previously prepared acetabulum. Once the cup 40 is firmly fitted, the user may actuate the holder-driver member 70 to release and remove the assembly 60 from the cup 40 without dislodging the cup 40.

It should be noted that the insertion and removal assembly 60 may be used for an acetabular cup or socket prosthesis 40 which is either press fitted or cemented to the acetabulum. The assembly 60 may be made of stainless steel, chrome steel, cobalt steel or titanium to have dimensions and weight generally acceptable to orthopaedic surgeons or users, and to withstand high temperatures necessary for sterilization prior to use. The design of the assembly 60 is such that the assembly 60 holds the acetabular cup 40 firmly so that even within the generally boney and narrow acetabulum, the cup 40 can be maneuvered to obtain ideal alignment. Furthermore, the assembly 60 is designed so that it can be generally easy to use.

Considering FIGS. 10 and 11, FIGS. 10 and 11 are fragmentary side views of a partially assembled acetabular cup prosthesis insertion and removal assembly 60, without the acetabular cup or socket prosthesis and the alignment guide assembly. The insertion and removal assembly 60 includes a holder-driver member 70 with a head 72 connected to one end and a bayonet coupler 80 secured to the other end.

The holder-driver member has first and second tubular portions 74, 76, and a linking member 78 that connects the tubular portions 74, 76 by welding or the like. The tubular portions 74, 76 are aligned such that a support extension 100 may be passed through the first tubular portion 74 into the second tubular portion 76.

The support extension 100 has a first threaded end portion 102. A securing member 104 is secured to the first threaded end portion 102 to mate with the interior surface 44 of the acetabular cup or socket prosthesis 40, which is shown in FIG. 3. In the preferred embodiment, the securing member 104 is substantially hemispherical, and includes a threaded aperture 106 to threadably engage the first threaded end portion 102 of the support extension 100.

Furthermore, the support extension 100 has a second threaded end portion 108, on which an adjustment member 110 is mounted after the support extension 100 is passed through the first tubular portion 74 of the holder-driver member 70. The adjustment member 110 includes a bore 112 which is substantially threaded to engage the second threaded portion 108 of the support extension 100. The adjustment member 110 also includes an adjusting knob 114 that a user may turn to extend or retract the support extension 100. The adjustment member 110 is preferably located within the area or space 79 defined and bounded by the linking member 78 so that the user may easily access the adjusting knob 114.

The user may selectively turn the adjusting knob 114 counterclockwise to retract or move the support extension 100 backward toward the direction of the second tubular portion 76 of the holder-driver member 70. When the support extension 100 is fully retracted, as shown in FIG. 10, a portion of the extension 100 protrudes into the second tubular portion 76. Furthermore, the securing member 104 mounted on the support extension 100 preferably contacts the bayonet coupler 80 and prevents further retraction of the extension 100.

The user may also turn the adjusting knob 114 clockwise to extend or move the support extension 100 forward toward the direction of the bayonet coupler 80. A detent 120 is inserted through the first tubular portion 74 and protrudes into an indented portion 105 of the support extension 100. The indented portion 105 is bounded by first and second side walls 107, 109. When the support extension 100 is fully extended, as shown in FIG. 11, the detent 120 contacts the second side wall 109 and prevents further extension of the extension 100.

As shown in FIGS. 10 and 11, a bayonet coupler 80 is secured to one thread end portion 75 of the holder-driver member 70. The coupler 80 has a bore 84, shown in FIGS. 10, 11, 15, and 16, through which the support extension 100 may be passed. In the preferred embodiment, the bore 84 is substantially threaded to allow the coupler 80 to be threadably secured to the threaded end portion 75 of the holder-driver member 70.

Turning now to FIGS. 13, 14, 15, and 16, the bayonet coupler 80 has a body portion 82 and fingers 86 extending from the body portion 82. The acetabular cup 40 has a plurality of recesses 42, as shown in FIG. 3. The fingers 86 on the bayonet coupler 80 are adapted to reach into the recesses 42 of the acetabular cup 40 to grip the cup 40. In the preferred embodiment, the bayonet coupler 80 includes three fingers 86 to reach into three recesses 42 on the acetabular cup 40. In practice, two or more fingers may be provided to engage a corresponding number of recesses on the acetabular cup.

Figure 13:
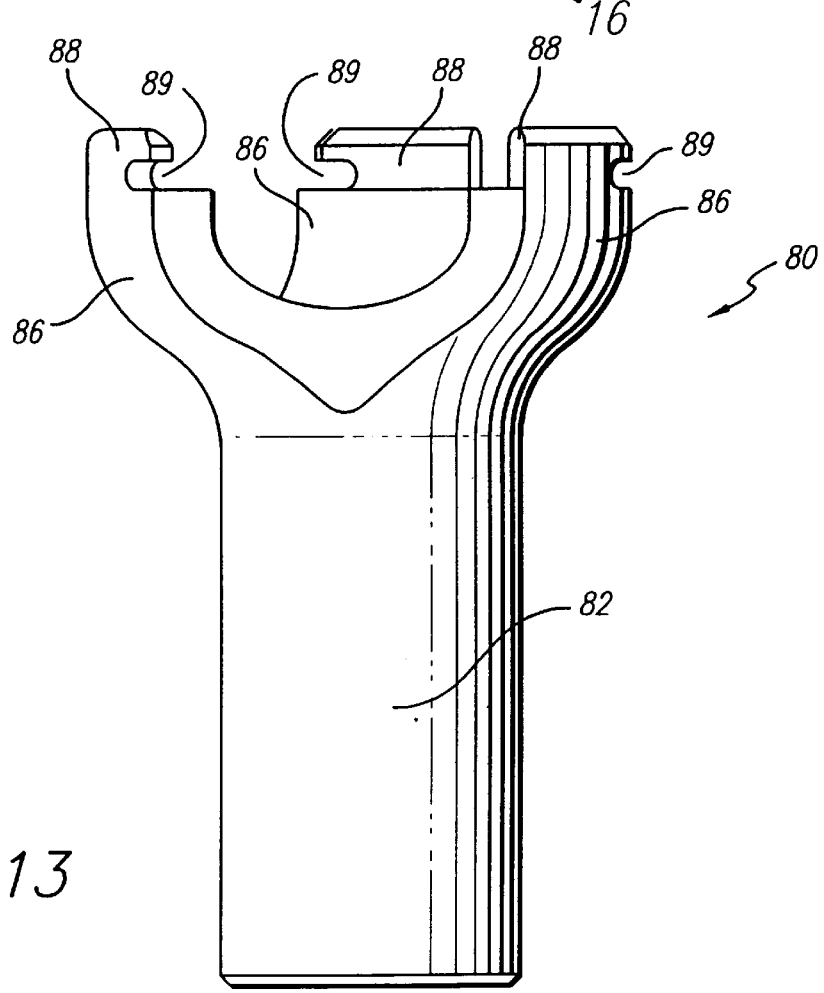
FIG. 13 is a front view of an exemplary bayonet coupler.

To attach the acetabular cup 40 to the bayonet coupler 80, the user may first insert the tips 88 of the coupler's fingers 86 into the cup's recesses 42. The user may then turn the cup 40 clockwise so that the indents 89 on the tips 88 of the coupler's fingers 86, which are shown in FIGS. 13 and 16, engage portions 43 of the cup's edge adjacent to the cup's recesses 42, which are shown in FIGS. 3 and 5. The user may finally turn the knob 114 on the adjustment member 110, which is shown in FIGS. 10 and 11, to extend the support extension 100 so that the securing member 104 mounted on the extension 100 mates with the interior surface 44 of the acetabular cup 40, which is shown in FIG. 3. When the securing member 104 mates with the cup's interior surface 44, a biasing force is applied to the cup 40 to urge the cup 40 away from the bayonet coupler 80, thereby firmly holding the cup 40 onto the coupler 80 for insertion, alignment, and impaction. Furthermore, the securing member 104 and the support extension 100 braces against the cup 40 and provides additional structural support as the user impacts the holder-driver member 70 to seat the cup in the patient's acetabulum.

Returning to FIGS. 10 and 11, an enlarged head 72 is formed on the other end of the holder-driver member 70 and is generally shaped to provide an ideal impacting surface. After the cup 40 is properly positioned to achieve an optimal alignment, the user may firmly tap the head 72 with an impacting tool, such as a mallet (not shown), to force or press fit the acetabular cup 40 into the patient's acetabulum. Following impaction, the user may rotate the assembly 60 counterclockwise to release the cup 40 from the bayonet coupler 80 and remove assembly 60 without disturbing the cup 40.

Turning now to FIG. 17, FIG. 17 shows an exploded perspective view of an alignment guide assembly 90. The alignment guide assembly 90 includes a body 92 and guiding members or arms 94. The body 92 has a central axial bore 96 with a diameter that can be adjusted by turning adjustment screws 98. The user may mount the alignment guide assembly 90 on the holder-driver member 70, as shown in FIG. 9, by passing the member 70 through the axial bore 96. In the preferred embodiment, the arms 94 have polygonal shaped ends 99 that can be inserted in polygonal apertures 97 of the screws 98 to turn the screws 98 to adjust the diameter of the bore 96.

The body 92 also includes threaded and angled apertures 93, 95 to receive the arms 94 at predetermined angles to help the user properly align the acetabular cup. The acetabular cup is normally inserted into the acetabulum of a patient lying horizontally on his or her side, with the acetabular cup being directed at tilted angles of approximately forty two degrees upward and twenty degrees from the front. Thus, in the preferred embodiment, apertures 93 are angled at approximately twenty degrees, and aperture 95 is angled at generally forty two degrees. With the patient lying on one side, the surgeon orients the arms vertically or horizontally, and thus has the assembly properly oriented for mounting the acetabular cup.

Figure 14:
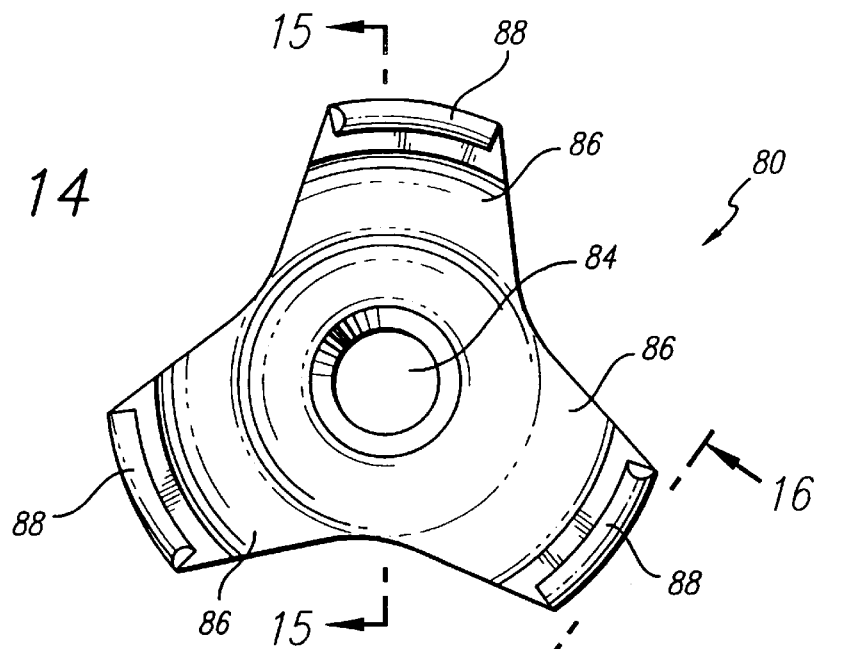
FIG. 14 shows a top view of the bayonet coupler shown in FIG. 13.

Turning now to FIG. 12, FIG. 12 is a side plan view of a slap-hammer or extractor 120 for removing the acetabular cup 40. The cup 40 should typically be removed if it is initially inserted in the acetabulum incorrectly. The extractor 120 includes a body 122 which has a stop 124 mounted on one end, a threaded portion 126 at the opposite end, and a handle 128 that is slidably secured to the body 122. To use the extractor 120, the user may first insert the threaded portion 126 of the extractor 120 into the thread aperture 73 in the head 72 of the holder-driver member 70, which is shown in FIGS. 10 and 11, to secure the extractor 120 to the holder-driver member 70. The user may then insert the fingers 86 of the bayonet coupler 80, which are shown in FIGS. 13–15, into the recesses 42 of the acetabular cup 40, which are shown in FIG. 3, to hold the cup 40 onto the coupler 80. To actuate the extractor 120, the user should slide the handle 128 toward the stop 124 with sufficient force, so that as the handle 128 contacts the stop 124, a sufficient shock is applied to the acetabular cup 40 to dislodge the it from the acetabulum. After the cup 40 is dislodged, the user may relocate and reorient it.

Although the present invention has been described in terms of the preferred embodiment above, numerous modifications and/or additions to the above-described preferred embodiment would be readily apparent to one skilled in the art. Thus, by way of example and not of limitation, the adjustment member is preferably mounted on the outer end of the extension. However, the adjustment member may instead be secured to the holder-driver member. As another example, the insertion and removal assembly may be used with an acetabular cup which is either press fitted or cemented to the acetabulum. As an additional example, the assembly may be made of stainless steel, chrome steel, cobalt steel, or titanium to have dimensions and weight generally acceptable to the users, and configured to accommodate sterilization prior to use. It is also noted that minor differences involving mechanical variations are within the scope of the invention, for example, using external threads instead of internal threads, and the use of an overcenter spring mechanism instead of mating threads to advance the member 104 into engagement with the acetabular cup 40. Accordingly, the present invention is not limited to the specific embodiment illustrated and described hereinabove.

What is claimed is:

1. In a metal-to-metal surface replacement hip prosthesis, the combination comprising:

an acetabular or socket prosthesis formed of biocompatible metallic material in substantially hemispherical configuration, having a thickness in the order of three millimeters to one centimeter, said prosthesis having an outer surface of rough metallic particulate material to encourage bone ingrowth, and an exposed edge, said edge having recesses therein with the recesses extending inward from said edge and further extending laterally into the body of said prosthesis, said prosthesis being formed substantially entirely of said metallic material;

a bayonet coupler having fingers for extending into said recesses;

a holder-driver member mechanically secured to said bayonet coupler;

a securing member movably mounted onto said holder-driver member for engaging said prosthesis to apply a biasing force to urge said prosthesis away from said coupler to thereby firmly hold said prosthesis onto said coupler, said securing member having a smooth outer surface for engaging said hemispherical configuration;

said holder-driver member having an enlarged head for receiving impacts and for applying the resultant force through the bayonet coupler to the exposed edge of said prosthesis to mount said prosthesis into the hip joint of the patient; and a wholly metallic surface type femoral prosthesis having a spherical outer surface for mating engagement with said acetabular prosthesis with close tolerances.

2. A combination as defined in claim 1 wherein said holder-driver member has a central axis, and further comprising at least one guiding arm mounted onto said holder-driver member, at a predetermined angle relative to the axis of said holder-driver member and said prosthesis, to accurately locate said prosthesis as it is being mounted in place.

3. A combination as defined in claim 1 wherein said prosthesis is approximately 5 mm thick.

4. A combination as defined in claim 1, wherein said femoral prosthesis has an outer spherical surface to mate with a substantially spherical inner surface of said acetabular prosthesis, with a clearance in the range of approximately 125 to 250 microns to permit lubrication by a patient's synovial fluid.

5. A combination as defined in claim 1 wherein said femoral prosthesis has an outer spherical surface to mate with a substantially spherical inner surface of said acetabular or socket prosthesis, with a tolerance in the range of approximately 1 to 5 microns.

6. A method of replacing a hip joint, comprising the steps of:

providing a substantially hemispherical acetabular cup prosthesis having (1) an outer surface of rough metallic particulate material to encourage bone ingrowth, (2) a substantially smooth inner surface, and (3) an edge having recesses extending inward from said edge and further extending laterally into said prosthesis;

providing a coupler having fingers for extending into said recesses of said acetabular cup prosthesis to secure said cup prosthesis to said coupler;

securing a holder-driver member, which has a head generally shaped to receive impacts, to said bayonet coupler;

mounting a support extension having an enlarged head onto said holder-driver member for engaging said acetabular cup prosthesis to apply a biasing force to urge said cup prosthesis away from said coupler to firmly hold said prosthesis onto said coupler;

attaching an alignment guide assembly to said holder-driver member;

inserting said acetabular cup prosthesis into a patient's acetabulum while using said alignment guide assembly to accurately locate and orient said cup prosthesis within the acetabulum; and impacting said head of said holder-driver member to press fit said cup prosthesis in the acetabulum.

7. A method as claimed in claim 6, further comprising the step of connecting an extractor to said holder-driver member for removing said prosthesis from a patient's acetabulum.

8. A method as claimed in claim 6, further comprising the step of providing an alignment guide assembly having a body and guiding arms attached to said body at predetermined angles relative to the axis of said holder-driver member to facilitate accurate placement of said cup prosthesis.

9. A method as claimed in claim 6, further comprising forming said cup prosthesis using a biocompatible metallic material.

10. In combination:

an acetabular or socket prosthesis formed of biocompatible metallic material in substantially hemispherical configuration, having a thickness in the order of three millimeters to one centimeter, said prosthesis having an outer surface of rough metallic particular material to encourage bone ingrowth, and an exposed edge, said edge having recesses therein with the recesses extending inward from said edge and further extending laterally into the body of said prosthesis;

a bayonet coupler having fingers for extending into said recesses;

a holder-driver member mechanically secured to said bayonet coupler;

a securing member movably mounted onto said holder-driver member for engaging said prosthesis onto said coupler;

said holder-driver member having an enlarged head for receiving impacts for mounting said prosthesis into the hip joint of the patient; and a slap-hammer removably mounted to said holder-driver member for removing said prosthesis for relocation or reorientation of said prosthesis.

11. In combination:

an acetabular or socket prosthesis formed of biocompatible metallic material in substantially hemispherical configuration, having a thickness in the order of three millimeters to one centimeter, said prosthesis having an outer surface of rough metallic particulate material to encourage bone ingrowth, and an exposed edge, said edge having recesses therein with the recesses extending inward from said edge and further extending laterally into the body of said prosthesis;

a bayonet coupler having fingers for extending into said recesses;

a holder-driver member mechanically secured to said bayonet coupler;

a securing member movably mounted onto said holder-driver member for engaging said prosthesis to apply a biasing force to urge said prosthesis away from said coupler to thereby firmly hold said prosthesis onto said coupler;

said holder-driver member having an enlarged head for receiving impacts for mounting said prosthesis into the hip joint of the patient; and said prosthesis having a flat circular edge, wherein three recesses are provided, and wherein these three recesses extend inwardly away from said edge, and laterally around and below said edge and break through the outer surface of said prosthesis.

12. In combination:

an acetabular or socket prosthesis formed of biocompatible metallic material in substantially hemispherical configuration, having a thickness in the order of three millimeters to one centimeter, said prosthesis having an outer surface of rough metallic particulate material to encourage bone ingrowth, and an exposed edge, said edge having recesses therein with the recesses extending inward from said edge and further extending laterally into the body of said prosthesis;

a bayonet coupler having fingers for extending into said recesses;

a holder-driver member mechanically secured to said bayonet coupler;

a securing member movably mounted onto said holder-driver member for engaging said prosthesis to apply a biasing force to urge said prosthesis away from said coupler to thereby firmly hold said prosthesis onto said coupler;

said holder-driver member having an enlarged head for receiving impacts for mounting said prosthesis into the hip joint of the patient; and said securing member having a generally hemispherical shape, and being secured to a support extension that is movably mounted onto said holder-driver member.

13. A method of replacing a hip joint using surface type thin wholly metallic prosthesis comprising the steps of:

providing a substantially hemispherical wholly metallic acetabular cup prosthesis having (1) an outer surface of rough metallic particulate material to encourage bone ingrowth, (2) a substantially smooth inner surface, (3) edge having recesses extending inward from said edge and further extending laterally into said prosthesis; and (4) a thickness in the order of three to ten millimeters;

providing a coupler having fingers for extending into said recesses of said acetabular cup prosthesis to secure said cup prosthesis to said coupler;

said coupler having secured thereto, a holder-driver member which has a head generally shaped to receive impacts;

mounting a support extension having an enlarged head onto said holder-driver member for engaging said acetabular cup prosthesis to apply a biasing force to urge said cup prosthesis away from said coupler to firmly hold said prosthesis onto said coupler;

inserting said acetabular cup prosthesis into a patient's acetabulum;

impacting said head of said holder-driver member and applying the resultant force through said coupler to the exposed edge of said prosthesis to press fit said cup prosthesis in the acetabulum; and mounting a surface type all metallic femoral prosthesis to mate with said cup prosthesis.

* * * * *

UNITED STATES PATENT AND TRADEMARK OFFICE
Certificate

Patent No. 6,063,124                                                                               Patented: May 16, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Harlan C. Amstutz, Pacific Palisades, CA (US); and Albert L. Lippincott III, Prior Lake, MN (US).

Signed and Sealed this Twelfth Day of October 2010.

*EDUARDO C. ROBERT*
*Supervisory Patent Examiner*
*Art Unit 3733*
*Technology Center 3700*